(12) United States Patent
Ensley

(10) Patent No.: US 6,872,552 B2
(45) Date of Patent: Mar. 29, 2005

(54) METHOD OF RECONSTITUTING NUCLEIC ACID MOLECULES

(76) Inventor: Burt D. Ensley, PMP 1319, 2675 W. Highway 89A, Sedona, AZ (US) 86336

( * ) Notice: Subject to any disclaimer, the term of this patent is extended or adjusted under 35 U.S.C. 154(b) by 421 days.

(21) Appl. No.: 09/794,190

(22) Filed: Feb. 27, 2001

(65) Prior Publication Data

US 2003/0077581 A1 Apr. 24, 2003

Related U.S. Application Data

(60) Provisional application No. 60/185,723, filed on Feb. 29, 2000.

(51) Int. Cl.$^7$ .............................................. C12P 19/34
(52) U.S. Cl. ..................................... 435/91.2; 435/91.1
(58) Field of Search ................................ 435/91.1, 91.2

(56) References Cited

U.S. PATENT DOCUMENTS 4,683,202 A * 7/1987 Mullis ........................ 435/91.2
5,750,335 A    5/1998 Gifford .......................... 435/6

FOREIGN PATENT DOCUMENTS

| EP | 0 721 016 | 7/1996 |
|---|---|---|
| WO | WO 93/09250 | 5/1993 |
| WO | WO 95/21271 | 8/1995 |
| WO | WO 97/31256 | 8/1997 |
| WO | WO 98/06830 | 2/1998 |
| WO | WO 00/56927 | 9/2000 |

OTHER PUBLICATIONS

Skryabin et al., Nucleic Acids Research, vol. 18, No. 14, 4289 (19990).*
Hsu, et al., "Visualization of Novel Simian Virus 40 DNA Recombination Intermediates Induced by Ultraviolet Light Irradiation", *Nucleic Acids Research*, 19(25): 7193–7199, 1991.
Komori, et al., "A Holliday Junction Resolvase from Pyrococcus Furiosus: Functional Similarity to *Escherichia coli* RuvC Provides Evidence for Conserved Mechanism of Homologous Recombination in Bacteria, Eukarya, and Archaea", *Proc. Natl. Acad. Sci., USA*, 96: 8873–8878, 1999.
Majesky et al., "Rat Carotid Neointimal Smooth Muscle Cells Reexpress a Developmentally Regulated mRNA Phenotype During Repair of Arterial Injury", XP–000995806.
Meselson, et al., "A General Model for Genetic Recombination", *Proc. Nat. Acad. Sci, USA*, 72(1): 358–361, 1975.
Orr–Weaver, et al., "Yeast Transformation: A Model System for the Study of Recombination", *Proc. Natl. Acad. Sci. USA*, 78(10): 6354–6358, 1981.
Sekiguchi, et al., "Resolution of Holliday Junctions by Eukaryotic DNA Topoisomerase I", *Proc. Natl. Acad. Sci. USA*, 93: 785–789, 1996.
Szostak, et al., "The Double–Strand–Break Repair Model of Recombination", *Cell.* 33: 25–35, 1983.
Vrhovski, et al., "Biochemistry of Tropoelastin", Review, XP–000996163.
International Search Report issued for corresponding PCT application PCT/US01/06427.

\* cited by examiner

*Primary Examiner*—Terry McKelvey
*Assistant Examiner*—Nancy T. Vogel
(74) *Attorney, Agent, or Firm*—Brenda Herschbach Jarrell; Charles E. Lyon; Choate, Hall & Stewart LLP

(57) ABSTRACT

The present invention provides a system for reconstituting nucleic acid molecules that have been degraded but still contain useful genetic information. The present invention uses, as a template for reconstituting degraded nucleic acids in a biological sample, nucleic acids from a genetically related or identical organism having a sequence homologous to the degraded nucleic acids. After hybridization of the degraded nucleic acids to the template, regions of the degraded nucleic acids that are missing in the duplex containing template nucleic acid molecules hybridized to degraded nucleic acids are filled in with nucleotides using the intact nucleic acid molecule as a template. The newly formed strand of nucleic acid is used as the template for a subsequent step of hybridization to degraded nucleic acid molecules. Regions of degraded nucleic acids that are missing in the duplex are again filled in with nucleotides using the newly formed nucleic acid as the new template. The process is repeated until the newly formed nucleic acid molecules are substantially representative of the nucleic acids from the genome of the species from which the degraded sample is obtained.

14 Claims, 3 Drawing Sheets

METHOD OF RECONSTITUTING NUCLEIC ACID MOLECULES

PRIORITY INFORMATION

This application claims priority under 35 U.S.C. §119(e) to the U.S. provisional patent application Ser. No. 60/185,723 by Ensley filed on Feb. 29, 2000, which is incorporated herein by reference in its entirety.

BACKGROUND OF THE INVENTION

The use of DNA in forensics is one of the most powerful tools available to law enforcement officials, prosecutors, and defendants. One use of DNA evidence has been to prove conclusively that DNA samples obtained from a crime scene did not originate from a suspect or from a person wrongly convicted of the crime. For example in several highly publicized cases, persons on death row have been exonerated from their crimes based primarily on evidence provided by DNA analysis of biological samples found at the crime scene. In fact, the state of Illinois has recently issued a moratorium on capital punishment in the state as a result of convicted persons on death row freed on the basis of DNA evidence. In these cases, DNA evidence can determine with absolute certainty that two DNA samples originated from two different individuals and not from the same individual.

Conversely, to determine that two DNA samples originated from the same individual, DNA analysis can provide an extremely high probability of a match. However, it can not be determined with absolute certainty that two DNA samples originated from the same individual.

Other examples of the use of DNA in forensics include identifying victims of crime and accidental catastrophes. In many cases, DNA at crime scenes or from natural or accidental catastrophes is degraded, thus rendering analyses of the DNA extremely difficult. One of the many techniques used in the analysis of DNA in forensics is restriction fragment length polymorphism (RFLP) analysis. Briefly, the analysis involves the cleavage of a sample of DNA by a restriction enzyme and the subsequent analysis of the size of the resulting cleavage fragments by polyacrylamide gel electrophoresis (PAGE). Since individuals contain regions of their genome that vary in size from person to person (variable number of tandem repeats; VNTR), a pattern of cleavage products on a gel representing the different sizes of cleavage products provides a DNA profile for each person.

When the pattern of cleavage products resulting from RFLP analysis differs for two different DNA samples, it is conclusive that the DNA samples originated from different people. However, when the pattern is identical for two DNA samples, a statistical analysis is necessary to determine the probability that the two samples are from the same person.

Unfortunately, a problem that arises with forensics analyses of DNA samples is the degradation and/or fragmentation of the DNA resulting from exposure to the environment and microorganisms which contain DNA endonucleases. The problem of degraded DNA is also faced by researchers who are analyzing the DNA obtained from frozen, extinct or extremely rare organisms. Therefore, there is a need for methods that reconstitute fragmented degraded DNA into DNA useful for genetic analysis and manipulation.

SUMMARY OF THE INVENTION

The present invention provides a method and system for reconstituting nucleic acid molecules that have been degraded but still contain genetic information. Useful applications of the present invention include but are not limited to reconstituting degraded nucleic acid molecules obtained from biological samples; nucleic acid molecules used in forensics where biological samples are found at crime scenes; nucleic acid molecules found in organisms whose species are extinct or endangered and found in a well preserved (or partially preserved) state such as in permafrost, tar, amber or as preserved in a museum; and/or nucleic acid molecules from deceased organisms where reconstitution of nuclear DNA, where establishing the original nucleotide sequence or genetic structure, or where cloning of the deceased organism is desirable.

In one aspect, the present invention provides methods of reconstituting fragmented nucleic acid molecules by utilizing as a template, nucleic acids from a genetically related organism with a high degree of nucleotide sequence homology in its genome. By using hybridization between a template strand and a strand from the fragmented nucleic acid sample, the template is used to reconstitute the relative order of the fragmented nucleic acids. Any gaps are filled in with nucleotide precursors. Subsequently, the fragmented strands are covalently linked using a polymerizing and/or ligating enzyme.

Degraded DNA from an organism may be reconstituted by using intact DNA from a related (or identical) genus or species as a template. Using the intact DNA from a genetically related organism as a template may be desirable when intact DNA from the original organism, species or genus is unobtainable such as for extinct species.

In a preferred embodiment of the present invention, intact DNA from a genetically related or identical organism is used as a template in the first step of reconstitution to piece together fragments from the degraded DNA. Hybridization of single stranded fragments to the template is performed under non-stringent conditions to allow full or partial duplex formation even in regions of partial complementarity. These regions may include mismatches and loops. After hybridization, regions of the template to which no DNA from the fragmented sample has hybridized are filled in and polymerized with added nucleotides.

The resulting newly formed polynucleotide strand contains both DNA from the degraded sample and added nucleotides whose polymerized sequence is complementary to a region of the template. Thus, the sequence of the newly formed polynucleotide is a hybrid of the sequence from the degraded sample and a sequence complementarity to the template. The newly formed hybrid polynucleotide is then used as a template in a subsequent round of hybridization under non-stringent conditions to piece together additional DNA molecules from the degraded sample. The second round of hybridization reconstitutes strands from the degraded sample complementary to the stranded reconstituted in the first round of reconstitution. This allows the reconstitution of nucleotide sequences even if one member of a base pair is degraded since the genetic information is maintained by the presence of at least one base of the base pair.

Again, missing sequences (gaps) are filled in with nucleotides and polymerized to form a second hybrid polynucleotide. The second hybrid polynucleotide will have a higher percentage of sequences found in the genome of the degraded DNA since there will be fewer regions containing gaps to fill in with nucleotides. The steps of hybrid polynucleotide template formation and reconstitution using the newly formed templates are reiterated until the sequence of the hybrid polynucleotide is representative or closely representative of the sequence found in the genome of the species from which the degraded sample is derived.

Reconstituted DNA is then used for sequence or genetic analysis or for construction of genes and/or chromosomes. Reconstructed genes and chromosomes can be used for a variety of purposes such as for nuclear transfer to clone an organism and for molecular genetic analysis.

Definitions

"Biological sample": As used herein, a "biological sample" means a material suspected of containing nucleic acids. Such biological samples include, as non-limiting examples, biological fluids such as blood, serum, plasma, sputum, lymphatic fluid, semen, vaginal mucus, feces, urine, and spinal fluid. Also included within the scope of the definition is biological tissue such as hair, skin, and fingernails. Other samples include cells, cultured cells, plants, food, forensic samples such as paper, fabrics and scrapings, water, sewage, medicinals, etc. When necessary, the sample may be pretreated with reagents to liquefy the sample and release the nucleic acids from binding substances. Such pretreatments are well known in the art.

"Nucleic acids": "Nucleic acids" are used herein to mean RNA and DNA. For nucleic acids in biological organisms, RNA and DNA are polynucleotides containing nitrogenous bases, and ribose sugars covalently linked through phosphodiester bonds. For purposes of the present invention, modifications to nitrogenous bases, ribose and deoxyribose sugars, and to phosphodiester bonds that do not disrupt hydrogen-bonded base pair formation are within the scope of the definition of nucleic acids. Nucleic acids in a biological sample includes without limitation genomic DNA, extrachromasomal DNA, mitochondrial DNA, messenger RNA, transfer RNA, ribosomal RNA, enzymatic RNA, nuclear nucleic acids and nucleolar nucleic acids. Methods of nucleic acid isolation and purification are widely known to those skilled in the art (see Sambrook et al. *Molecular Cloning: A Laboratory Manual*, Cold Spring Harbor Laboratory Press, Cold Spring Harbor, N.Y., 1989; and Ausubel et al. *Current Protocols in Molecular Biology*. John Wiley & Sons. New York. 1999, both incorporated herein by reference).

"Degraded": The term "degraded" is used herein to mean nucleic acid molecules that have been partially fragmented, have a low percentage of abasic sites, or have a low degree of modifications to the base, sugar and phosphate backbone. Preferably, but not necessarily, the average length of nucleic acid molecules from a partially fragmented sample is between 50 base pairs and 10 kilobase pairs. More importantly for purposes of the present invention, the average length of nucleic acid molecules should be greater than approximately six nucleotides.

The percentage of abasic sites in a degraded sample should not be at a level which results in degraded samples hybridizing to a region of a template that is not complementary to the original non-degraded nucleotide sequence of the nucleic acid in the sample. In addition, chemical modifications of a base or nucleotide that do not inhibit the ability of the base or nucleotide to form a stable (or transiently stable) hydrogen bonded base pair with its natural complement are acceptable. A stable hydrogen bonded base pair preferably has at least two hydrogen bonds. A modification of a base may reduce the stability of a base pair but still be a stable. For example, the loss of the 2-amino exocyclic group of guanine to form inosine reduces hydrogen bonding to cytosine. However, an inosine/cytosine base pair is stable with two hydrogen bonds.

The terms "complement" "complementary" or "complementarity" refer to the base pair scheme as set forth by Watson-Crick base pairing complementation. In a canonical Watson-Crick base pair, an adenine base in a nucleotide forms a base pair with a thymine base through two hydrogen bonds, and a guanine base forms a base pair with a cytosine base through three hydrogen bonds. For RNA, thymine bases are replaced with uracil bases.

A nucleic acid strand is complementary to another strand when the nucleotide sequence in the 5' to 3' direction contains complementary nucleotides to the complementary strand in the 3' to 5' direction. As is well known in the art, the natural directionality of strands in a duplex of two hybridized nucleic acid molecules is anti-parallel.

"Hybridization": As used herein to describe nucleic acids, the term "hybridization" refers to the formation of "Watson-Crick" hydrogen-bonded base pairs between two regions having partial or complete complementary nucleotide sequences. Those of ordinary skill in the art are capable of adjusting conditions of hybridization between nucleic acids to enhance or disrupt hybridization. For example, the stringency of conditions that permit hybridization between nucleic acids can be controlled by adjusting factors such as temperature, salt concentrations, detergent concentrations, and the presence of chemicals such as formamide.

The term "non-stringent" is used herein to mean hybridization conditions for the formation of double-stranded duplex nucleic acids wherein complementarity between the two strands is not 100%. Preferably complementarity exists between at least 90% of the sequences between the two strands. More preferably, complementarity exists between at least 95% of the sequences between the two strands. Most preferably, complementarity exists between at least 99% of the sequences between the two strands.

"Denature or denaturing": As used herein to describe nucleic acids, the term "denature" or "denaturing" refers to disruption of hydrogen-bonded based pairs between two regions of partial or complete complementary nucleotide sequences. Denaturation includes in its meaning the disruption of hybridization between two nucleic acid molecules (intermolecular) and hybridization between two complementary regions in one nucleic acid molecule (intramolecular secondary structure).

"Homologous or homology": As used herein to describe nucleic acids, the terms "homologous" and "homology" refer to the amount or percentage of identical nucleotides between two sequences when the position and identity of nucleotides are compared. Preferably, homology is present between the entire template and the degraded nucleic acid. More preferably for purposes of the present invention, homology is present between the template and degraded nucleic acid sample at regions of interest such as without limitation, genes, coding sequences, and regions of polymorphisms.

"Substantially identical": For purposes of the present invention, two nucleotide sequences are substantially identical if the sequences are at least 99.9% homologous. Preferably, substantially identical sequences are at least 99.99% homologous. Therefore, sequences that are 100% identical are also substantially identical.

DESCRIPTION OF CERTAIN PREFERRED EMBODIMENTS

Figure 1:
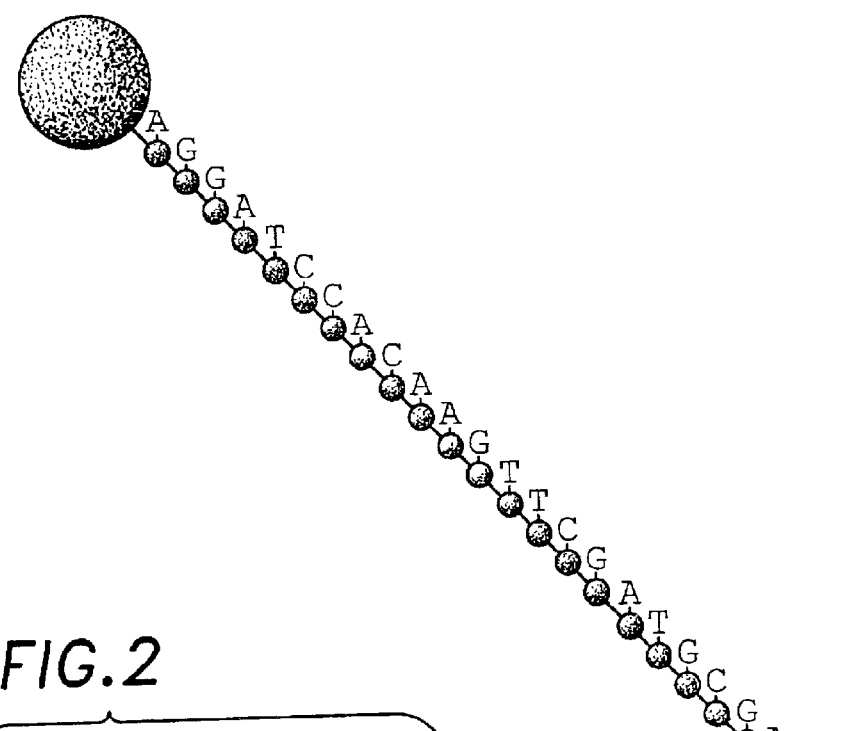
FIG. 1 depicts the immobilization of an intact single strand of DNA onto a solid support such as a bead. For reconstitution of degraded DNA from an extinct species, DNA is isolated from a modern species, denatured to produce single strands and immobilized, for example by linking the DNA to a solid substrate such as a bead.

The present invention provides a method and system for reconstituting degraded DNA using, as an initial template, DNA from an organism whose genome has a nucleotide sequence that is at least approximately 90% homologous with nucleotide sequences of interest from the degraded DNA. The present invention is particularly useful for reconstituting degraded DNA when the source of the intact DNA from the same organism or species is nonexistent or difficult to obtain. Of course, the present invention may still be practiced when intact DNA from the organism from which the degraded DNA was obtained is available. Any DNA which has been partially degraded may be reconstituted according to the present invention. Examples of applications of the invention include but are not limited to reconstituting DNA obtained from crime scenes, natural and accidental catastrophes, rare or extinct organisms, unique and valuable organisms (e.g., pets, races horses, genetically engineered animals such as mice, valuable livestock).

Methods of the present invention for reconstituting degraded DNA utilize the relatively high degree of nucleotide sequence homology between degraded DNA from unavailable organisms (i.e. criminals, deceased persons, missing persons, extinct species, endangered species, deceased animals) and DNA from another person, a relative, or an organism from a related genus or species.

In one embodiment, degraded DNA from a crime scene is reconstituted into intact DNA using template DNA from another person. Preferably but not necessarily, the template DNA is obtained from a relative of the person suspected of being the source of the degraded DNA (criminal suspect, missing person, victim etc.). Alternatively or additionally, the template DNA is obtained from an unrelated person. For example, the template DNA may be chosen from a set of templates whose sources originate from people with widely differing genetic backgrounds (e.g. Caucasian, Asian, African, European, native American, Middle Eastern etc.) Therefore, any bias in reconstituted DNA resulting from the source of template DNA may be reduced or eliminated.

Methods of analyses used in forensics and genetic testing such as paternity identification are well known in the art. One method involves the analysis of regions of genomic DNA having variable numbers of tandem repeats (VNTR). The analysis takes advantage of restriction fragment length polymorphism (RFLP) in the VNTR. Cleavage of genomic DNA by a restriction enzyme such as Hae III results in cleavage products of varying size which are separated and resolved using polyacrylamide gel electrophoresis (PAGE). The pattern of cleavage products from the VNTR is compared to the pattern from another DNA sample. A difference between the two patterns indicates that two DNA samples were derived from two different persons. Two identical patterns indicates that there is a probability the two samples were derived from the same person. The probability is determined in part by the number of VNTR loci examined. Since RFLP analysis examines the size of DNA, analysis of degraded DNA by RFLP is problematic. Therefore, the present invention is useful for reconstituting degraded DNA for analysis by RFLP.

In another embodiment, the method of the present invention is used to reconstitute degraded DNA from an extinct organism (including plants and animals) using as a template, DNA from a related organism that is not extinct. For example, genomic DNA from a present day tiger is likely to have sequence homology of between 97–99% when compared to the genomic DNA sequence of a saber tooth cat or saber tooth tiger. Furthermore, the genomic DNA sequence of the modern elephant is likely to have a high degree of homology when compared to the genome sequence of a woolly mammoth or a mastodon. These assumptions are supported by the fact that the genomic DNA sequence of *Homo sapiens* has an approximately 98.5% homology with modern day chimpanzees (*Pan troglodytes*) even though the two species evolutionarily diverged millions of years ago (Luke and Verma. Am J Phys Anthropol 1995 January; 96(1):63–71). Therefore, degraded DNA from extinct species can be reconstituted by using DNA from genetically related modern-day species as a template.

The present invention may also be utilized to reconstitute DNA from plants and animals considered to be endangered. For extremely rare species, it may be difficult to obtain cells and DNA from a live organism genetic analysis. However, a DNA sample from an extremely rare species may be obtained from a dead specimen and reconstituted according to the method of the present invention. After reconstitution, the genome of the animal can then analyzed. For an extensive list of endangered species, the United States Fish and Wildlife Service provides information on their website.

The present invention may also be utilized to reconstitute DNA from valuable, but deceased plants and animals that may be degraded, and therefore, required reconstitution for genetic analysis. Non-limiting examples of valuable plants and animals include livestock, race horses, show dogs, prized plants, pets and genetically engineered scientific tools such as cell lines and genetically engineered animals such as mice, goats and primates.

The present invention is also useful for reconstituting degraded DNA from extinct and rare plant species. For example, samples of vines and grapes from rare grapes (or where a living specimen is not obtainable) contain DNA samples which can be studied genetically. One example of a useful genetic analysis is the determination of the genetic relationship between a particular extinct or rare species of grapes and a related (or even unrelated) present day species of grapes from renowned vineyards.

In another non-limiting example of applications of the present invention, a plant such as rice may have an extinct or rare species which is particularly well-suited to adverse conditions such as weather and disease. However, the genetic origin of the trait responsible for the survival of the plant is unknown. Therefore, methods of the present invention may be used to reconstitute degraded nucleic acids samples from rare and extinct plant species for genetic analysis.

In yet another non-limiting example of applications of the present invention, degraded DNA from extinct organisms may be reconstituted and used to study and/or clone the extinct organism. With major advances in the technology of cloning through nuclear transfer, there are currently efforts underway to clone extinct species recovered from permafrost ground (New York Times, Oct. 5, 1999; Science Times Section). Since DNA recovered from these extinct organisms is likely to be degraded, it would be useful to be able to reconstitute molecules of DNA that have been degraded through exposure to the environment. Preferably, the method of the present invention is used to reconstitute DNA molecules from species that have become extinct in the past several thousand years. Such extinct species are more likely to have a genetically related modern day counterpart. Non-limiting examples of such extinct species include the saber toothed cat and tiger, the cave bear, the giant sloth, the woolly mammoth, the mastodon, the woolly rhinoceros, the dire wolf, the quagga, the carrier pigeon, the dodo bird, and the giant ostrich. (For a more extensive list of recent extinct species see Crowe, P. K. *The Empty Ark*. Charles Scribner's Sons, New York. 1967; See also, Day, D. *The Doomsday Book of Animals. A Natural History of Vanished Species*. Viking Press, New York. 1981). However, the present invention is not limited to recently extinct species since for example animals such as sharks and alligators have not drastically changed in 200 million years. Therefore, modern sharks and alligators are likely to be genetically closely related to extinct species which were alive hundreds of millions of years ago.

In a preferred embodiment of the present invention, DNA from a closely related genus or species is used as an initial template for hybridization in order to reconstitute fragmented DNA. Preferably, the genome of the genetically related organism has a sequence homology of at least 90% when compared to the sequence of the degraded sample. More preferably, the sequence homology is at least 95%. Most preferably, the sequence homology is at least 99%.

The method of the present invention relies on the ability to separate the template strand from the polymerized strand after polymerization of degraded fragments. In a preferred embodiment, the template DNA is first immobilized. Numerous methods of immobilization and attachment of DNA to a solid support are known and available to one or ordinary skilled in the art of nucleic acids chemistry (Ausubel et al. *Current Protocols in Molecular Biology*. John Wiley & Sons. New York. 1999; Sambrook et al., *Molecular Cloning: A Laboratory Manual*, Cold Spring Harbor Laboratory Press, Cold Spring Harbor, N.Y., 1989; Meinkoth and Wahl. *Anal. Biochem*. 138:267–84, 1984; all of which are incorporated herein by reference).

Preferably, the DNA is immobilized by attachment to a solid support such as a bead (FIG. 1). Attachment may be facilitated by methods using covalent or noncovalent interactions. Examples of non-covalent interactions include but are not limited to using biotin-streptavidin conjugation where a DNA sample is biotinylated and a solid support is coated with streptavidin (e.g. Dynabeads, Dynal Inc., Oslo, Norway). The binding constant for the interaction between biotin and streptavidin is on the order of $10^{14-15}$ and is ideally suited as a method of attachment to a solid support.

Intact template DNA may be segmented into large pieces to facilitate immobilization onto a solid support. However, it is not required since template DNA having modified nucleotides (e.g. biotinylated) that enable immobilization may be generated by a DNA polymerase without fragmentation. Generating large segments of DNA from the template may be performed by any method including sonication, enzymatic digestion and chemical fragmentation. Preferably if the template DNA is to be segmented into large pieces, sonication is used. Methods of fragmentation that do not introduce modifications to bases and nucleotides are preferred.

Figure 2:
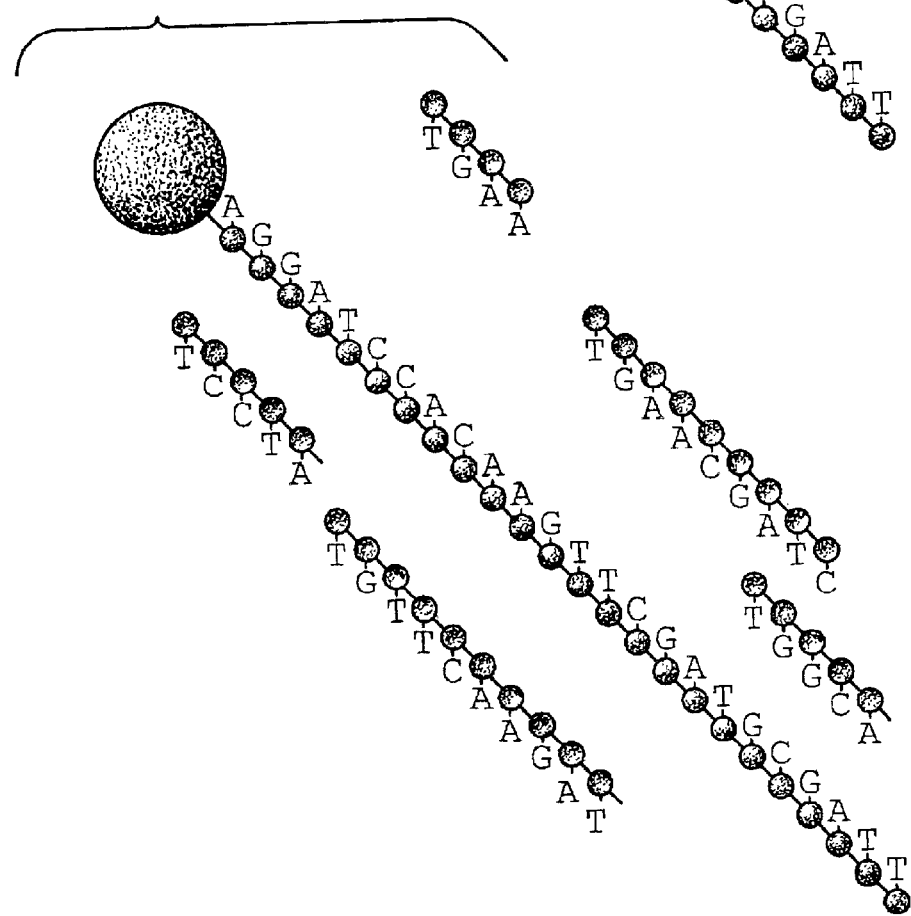
FIG. 2 depicts the addition of fragmented single stranded DNA to the immobilized template DNA. The immobilized DNA is mixed with a sample of DNA extracted from an environment containing the remains of a similar extinct species and allowed to anneal under "non-stringent" conditions.
Figure 3:
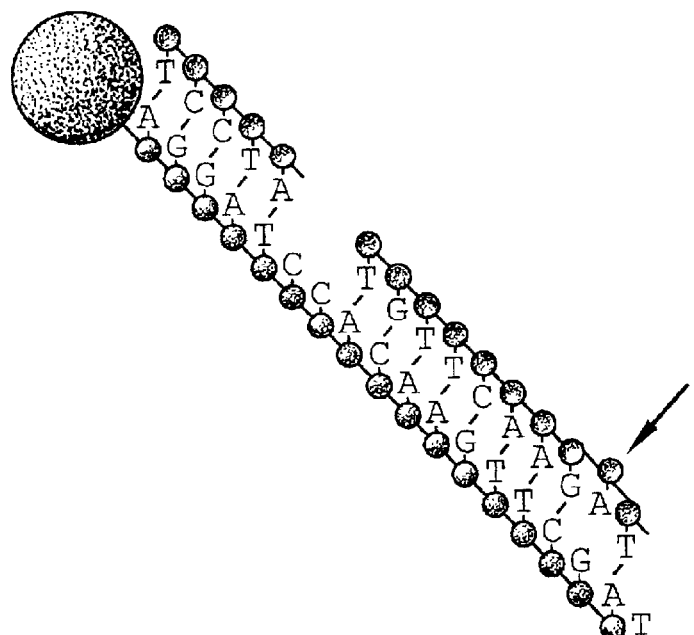
FIG. 3 depicts hybridization of the fragmented DNA to the immobilized template under non-stringent conditions to permit duplex formation in the presence of DNA base pair mismatches or loops. The DNA fragments form hydrogen bonds with the immobilized DNA and create a partial double strand. The fragments anneal under the chosen conditions even if an occasional base pair, shown with an arrow, is not an identical match with modern DNA. The DNA mismatch will occur an estimated once or twice per one hundred base pairs of sequence. This imperfect form of annealing will preserve the essential, unique DNA sequence of an extinct species while the DNA of a modern ancestor is used as the template.

The immobilized template DNA is denatured to produce single strands. DNA from the degraded sample is also denatured to produce single strands and hybridized to the immobilized template single-strand DNA (FIG. 2). Preferably the conditions for hybridization are non-stringent such that perfect complementary between a template strand and a strand from the degraded sample is not required for hybridization to occur. This will result in mostly duplex DNA containing mismatches and loops in regions of non-complementarity (FIG. 3). For reconstitution of degraded DNA from extinct species, DNA mismatches will occur on average about once or twice per every hundred base pairs of sequences. This is due to the approximately 1–2% difference in nucleotide sequence between the genome of the extinct species and the genome of the modern day related species.

One of ordinary skill in the art can modulate the stringency of hybridization according to known methods (Ausubel et al. *Current Protocols in Molecular Biology*. John Wiley & Sons. New York. 1999; Sambrook et al., *Molecular Cloning: A Laboratory Manual*, Cold Spring Harbor Laboratory Press, Cold Spring Harbor, N.Y., 1989). Preferably, conditions for hybridization are such that complementarity of at least 90% between two strands results in duplex formation. More preferably, conditions for hybridization are such that complementarity of at least 95% between two strands results in duplex formation. Most preferably, conditions for hybridization are such that complementarity of at least 99% between two strands results in duplex formation.

Figure 4:
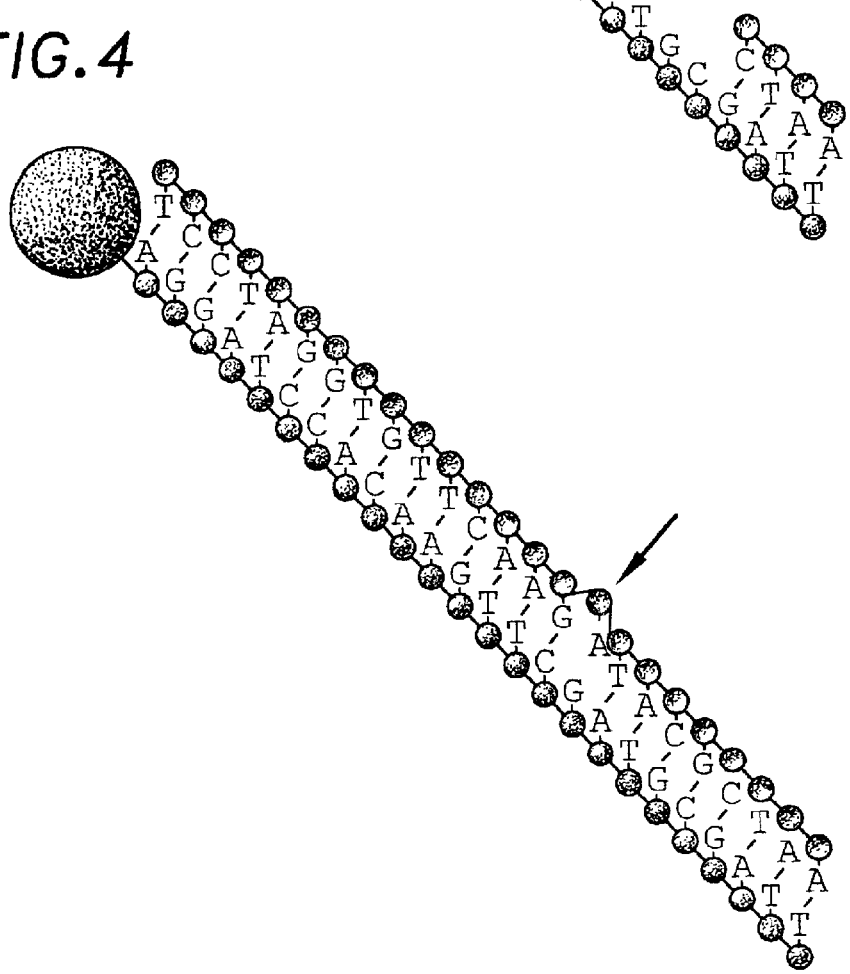
FIG. 4 depicts the polymerization of the previously fragmented single strands and nucleotides which are added. A DNA repair enzyme is used to fill in the "gaps" in the DNA sequence and create a complete second strand. Since the gaps will occasionally occur where there is an important difference in the DNA sequence between the ancient ancestor and the modern template, the first iteration of this process is likely to produce a new DNA that represents a hybrid between the DNA from the extinct species and DNA from the modern non-extinct species.

The formed partial duplex DNA will have regions (gaps) where no DNA from the degraded sample has hybridized to the intact template DNA from the related species. These regions will be "filled in" with nucleotides by polymerizing the nucleotides with the degraded single strand samples hybridized to the intact DNA. The correct nucleotide sequence to be polymerized is determined by the template (FIG. 4). Preferably polymerization proceeds enzymatically. More preferably, polymerization is facilitated by a DNA repair enzyme. Examples of DNA repair enzymes include but are not limited to the DNA polymerase β/DNA ligase I complex and bacterial DNA polymerase I and III. Thus the newly formed polynucleotide strand contains both nucleotides from the degraded DNA sample and nucleotides whose sequences are derived from the template DNA.

Figure 5:
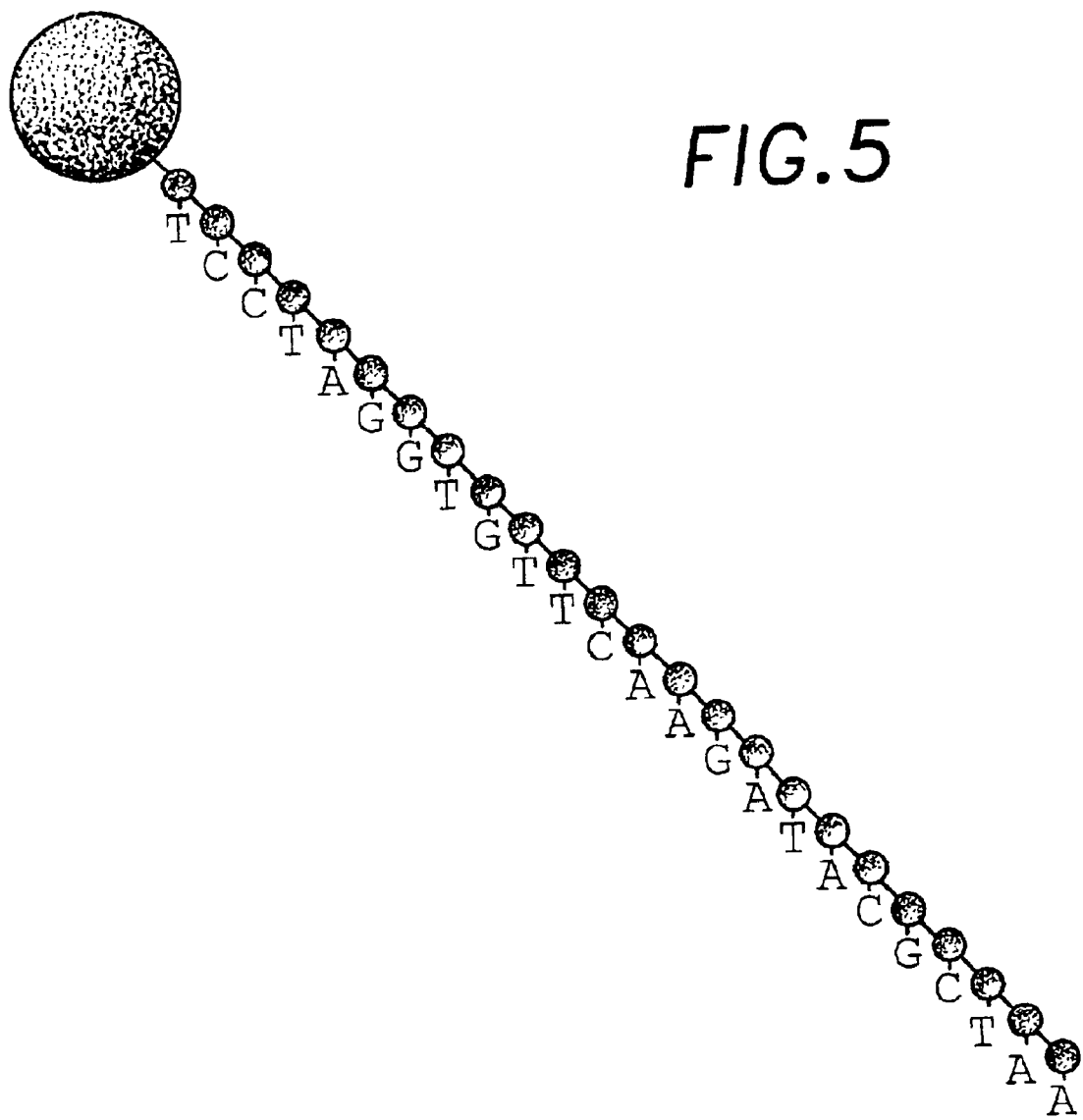
FIG. 5 depicts the newly synthesized strand of DNA which is a hybrid of previously degraded DNA and nucleotides complementary to the template DNA. The two DNA strands are separated by "melting" and the newly constructed strand is isolated from the modern template. The newly synthesized strand becomes the new template by immobilization on a solid support. The process of mixing and annealing fragments of degraded DNA, filling in missing portions with a DNA repair enzyme, and separating and immobilizing the new template DNA is repeated until the resulting DNA strand is likely to faithfully represent the DNA sequence of the extinct species, including all of the rare differences between the sequence of the original species and those of the modern template. The new sequence can now be used to construct intact genes and chromosomes representing the complete regenerated DNA of an extinct species for introduction into enucleated cells and subsequent development as embryos of formerly extinct species.

In a subsequent step, the resulting duplex is denatured and the newly formed nucleotide strand, containing sequences from the previously degraded DNA sample, is separated from the original template DNA (FIG. 5). Separation may be accomplished by any method known to those skilled in the art of nucleic acid purification. For example, the strand from intact DNA may be biotinylated and attached to magnetic beads coated with streptavidin which binds tightly to biotin. Under denaturing conditions, the strand from intact DNA may be magnetically separated from the newly polymerized strand containing previously degraded DNA.

The newly formed strand then serves as the template for a subsequent step of hybridization (FIG. 5). In the next step, additional degraded DNA extracted from the same sample or from the same species is denatured and hybridized to the new template which is immobilized on a solid support. Again, hybridization proceeds under non-stringent conditions to allow for base pair mismatches and loops. Any gaps that exist in regions where no DNA from the degraded sample has hybridized to the template are again filled in preferably by a DNA repair enzyme. The second newly formed strand will contain a higher percentage of DNA sequences from the genome of the species or organism that is the source of the degraded DNA. This may be due in part to the fact that degraded DNA which has lost one member of a base pair will still contain genetic information if either base is present in a single or double stranded DNA sample. If that one base is not detected by the first round of hybridization, then it will be detected in the second round of hybridization which seeks the complementary base of the degraded sample.

The steps of obtaining single stranded template, hybridizing to degraded DNA, filling in the gaps and isolating the newly formed strand are reiterated until the DNA strand is likely to faithfully represent the DNA sequence of the extinct species, including all of the rare differences between the sequence of the original species and those of the modern template. It is preferable that most of the degraded DNA is reconstituted since formation of natural or artificial chromosomes or genes may required coding and non-coding sequences (Wolffe. *Chromatin: Structure and Function*. Academic Press. 3rd edition. 1998; and references therein all of which are incorporated herein by reference). However, it is more preferable to reconstitute sequences related to transcription of genes (i.e. coding sequences, promoters, enhancers, repressor binding sites etc.) in order to maintain the proper synthesis of polypeptides necessary for producing a viable organism.

The reconstituted nucleic acid molecule may be used by those skilled in the art of nucleic acids chemistry and molecular biology for genetic analysis, to study expressed sequences and their polypeptide products, to study genetic evolution, and without limitation for reconstituting chromatin and intact chromosomes. Moreover, the reconstituted chromatin, the reconstituted chromosomes and reconstituted coding sequences may be used by those skilled in the art to clone organisms whose DNA was previously unavailable for cloning through nuclear transfer.

It is appreciated by those of ordinary skill in the arts that modifications to the methods of the present invention may be introduced without altering the inventive aspects of the present invention.

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:DNA
      isolated from a modern species

<400> SEQUENCE: 1
aggatccaca agttcgatgc gatt                                       24

<210> SEQ ID NO 2
<211> LENGTH: 4
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1
```

```
<400> SEQUENCE: 2 tgaa                                                                  4

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1

<400> SEQUENCE: 3 tgaacgatc                                                             9

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1

<400> SEQUENCE: 4 tggca                                                                 5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:DNA
      isolated from a modern species

<400> SEQUENCE: 5
aggatccaca agttcgatgc gatt                                           24

<210> SEQ ID NO 6
<211> LENGTH: 5
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1

<400> SEQUENCE: 6 tccta                                                                 5

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1

<400> SEQUENCE: 7
tgttcaagat                                                           10
```

```
<210> SEQ ID NO 8
<211> LENGTH: 5
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1

<400> SEQUENCE: 8 tccta                                                                     5

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern species of
      SEQ ID NO:1

<400> SEQUENCE: 9
tgttcaagat                                                               10

<210> SEQ ID NO 10
<211> LENGTH: 4
<212> TYPE: DNA
<213> ORGANISM: Artificial Sequence
<220> FEATURE:
<223> OTHER INFORMATION: Description of Artificial Sequence:DNA
      extracted from an environment containing the remains of an
      extinct species that is similar to the modern
      species of SEQ ID NO:1

<400> SEQUENCE: 10 ctaa                                                                      4

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:DNA isolated
      from a modern species

<400> SEQUENCE: 11
aggatccaca agttcgatgc gatt                                               24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Hybrid DNA
      prepared using a template DNA from a modern
      species and fragments of DNA from an extinct
      species that is similar to the modern species

<400> SEQUENCE: 12
tcctaggtgt tcaagatacg ctaa                                               24

<210> SEQ ID NO 13
<211> LENGTH: 24
<212> TYPE: DNA
<213> ORGANISM: Artificial Sequence
<220> FEATURE:
```

-continued

```
<223> OTHER INFORMATION: Description of Artificial Sequence:DNA isolated
      from a modern species

<400> SEQUENCE: 13
aggatccaca agttcgatgc gatt                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Hybrid DNA
      prepared using a template DNA from a modern
      species and fragments of DNA from an extinct
      specie that is similar

<400> SEQUENCE: 14
tcctaggtgt tcaagatacg ctaa                                            24
```

I claim:

1. A method of reconstituting a degraded nucleic molecule from a first organism comprising steps of:
   a) providing a sample comprising fragments of the degraded nucleic acid molecule, wherein, prior to being degraded, the nucleic acid molecule was double-stranded and the sample comprises fragments of each strand;
   b) providing a nucleic acid template comprising at least one strand of a nucleic acid molecule from a second organism, which second organism is sufficiently genetically related to the first organism that the template hybridizes with fragments of one strand of the degraded nucleic acid molecule;
   c) admixing the fragments and the template under conditions such that appropriate fragments hybridize to the template;
   d) contacting the hybridized nucleic acids from step c) with nucleotide precursors and an appropriate polymerizing and ligating enzyme or enzymes such that the hybridized fragments are extended and a product strand is synthesized, which product strand consists of the hybridized fragments linked to one another via extended nucleotides complementary to the template;
   e) isolating the product strand;
   f) performing steps a) through f) using the isolated product strand from step e) as a new template strand; and
   g) repeating steps a) through f) until the nucleotide sequence of the product strand produced in step d) is substantially identical to the nucleotide sequence of the strand produced in a second previous execution of steps a) through f).

2. The method of claim 1, wherein in the steps of providing, the nucleic acids are DNA or RNA.

3. The method of claim 1, wherein in the step of contacting, the polymerizing and ligating enzyme or enzymes are selected from the group consisting of DNA polymerases, DNA ligases, and DNA repair enzymes.

4. The method of claim 1, wherein in the step of providing a template, the template is immobilized through attachment to a solid support.

5. The method of claim 1, wherein in the step of providing a sample comprising fragments of the degraded nucleic acid molecule, the sample is evidence obtained in a crime scene.

6. The method of claim 1, wherein in the step of providing a sample comprising fragments of the degraded nucleic acid molecule, the sample is a biological sample obtained from a natural or an accidental catastrophe.

7. The method of claim 1, wherein in the step of admixing, the fragments are hybridized to the template under conditions of stringency that permits duplex formation containing gaps and mismatches.

8. The method of claim 1, wherein in step g), steps a) through f) are repeated until the product strand produced in step d) comprises a nucleotide sequence which is at least 99.9% homologous to the sequence of the strand produced in a second previous execution of steps a) through f).

9. The method of claim 1, wherein in step g), steps a) through f) are repeated until the product strand produced in step d) comprises a nucleotide sequence which is 100% homologous to the sequence of the strand produced in a second previous execution of steps a) through f).

10. The method of claim 1, wherein in the step of providing a template, the second organism is from a related genus.

11. The method of claim 1, wherein in the step of providing a template, the first and second organisms belong to the same genus.

12. The method of claim 1, wherein in the step of providing a template, the second organism is from a related species.

13. The method of claim 1, wherein in the step of providing a template, the first and second organisms belong to the same species.

14. The method of claim 1, wherein in the step of providing a template, the first and second organisms are the same.

* * * * *

UNITED STATES PATENT AND TRADEMARK OFFICE
CERTIFICATE OF CORRECTION

PATENT NO. : 6,872,552 B2
DATED : March 29, 2005
INVENTOR(S) : Burt D. Ensley

It is certified that error appears in the above-identified patent and that said Letters Patent is hereby corrected as shown below:

Column 15,
Lines 49-50, "performing steps a) through f) using the isolated product strand from step e) as a new template strand" should read as -- performing steps a) through e) using the isolated product strand from step e) as a new template strand --.

Signed and Sealed this

Twelfth Day of July, 2005

JON W. DUDAS
*Director of the United States Patent and Trademark Office*